(12) United States Patent
Sun et al.

(10) Patent No.: US 11,779,366 B2
(45) Date of Patent: Oct. 10, 2023

(54) ULTRASONIC OSTEOTOME BIT

(71) Applicant: BEIJING SMTP TECHNOLOGY CO., LTD., Beijing (CN)

(72) Inventors: Yu Sun, Beijing (CN); Qun Cao, Beijing (CN); Songtao Zhan, Beijing (CN)

(73) Assignee: Beijing SMTP Technology Co., Ltd., Beijing (CN)

( * ) Notice: Subject to any disclaimer, the term of this patent is extended or adjusted under 35 U.S.C. 154(b) by 797 days.

(21) Appl. No.: 16/758,007

(22) PCT Filed: Sep. 14, 2018

(86) PCT No.: PCT/CN2018/105781
§ 371 (c)(1),
(2) Date: Apr. 21, 2020

(87) PCT Pub. No.: WO2019/095831
PCT Pub. Date: May 23, 2019

(65) Prior Publication Data
US 2020/0289147 A1    Sep. 17, 2020

(30) Foreign Application Priority Data

Nov. 14, 2017  (CN) .......................... 201711118873.2

(51) Int. Cl.
*A61B 17/32* (2006.01)
*A61B 17/16* (2006.01)

(52) U.S. Cl.
CPC .. *A61B 17/320068* (2013.01); *A61B 17/1644* (2013.01); *A61B 2017/1602* (2013.01);
(Continued)

(58) Field of Classification Search
CPC . A61B 17/16; A61B 17/1604; A61B 17/1615; A61B 17/1644; A61B 17/1655;
(Continued)

(56) References Cited

U.S. PATENT DOCUMENTS 4,921,476 A    5/1990  Wuchinich
5,385,572 A    1/1995  Nobles et al.
(Continued)

FOREIGN PATENT DOCUMENTS

CN    102143715 A    8/2011
CN    103153216 A    6/2013
(Continued)

OTHER PUBLICATIONS

International Search Report (English Translation) dated Nov. 7, 2018 in International Application No. PCT/CN2018/105781, 2 pages.
(Continued)

*Primary Examiner* — Ashley L Fishback
(74) *Attorney, Agent, or Firm* — Kilpatrick Townsend & Stockton LLP

(57) ABSTRACT

An ultrasonic osteotome bit, comprising a bit bar (1), a bit body (3), and a bit grinding portion (2) located at a front end of the ultrasonic osteotome bit. The bit grinding portion (2) is in the shape of a triangular pyramid, the bottom face of the triangular pyramid is the rear end of the bit grinding portion (2), and the tip of the triangular pyramid directly facing the bottom face is the front end of the bit grinding portion (2). One end of the bit bar (1) is connected to the rear end of the bit grinding portion (2), and the other end of the bit bar (1) is connected to the bit body (3). Two of the three lateral pyramidal faces of the triangular pyramid are respectively used as a first grinding face (21A) and a second grinding face (21B). By means of the ultrasonic osteotome bit, a
(Continued)

normal bone-grinding operation can be completed, and since the front end thereof is small in area, the grinding speed is high. In addition, owing to the design in which the front end is small while the rear end is large, a good visual field can be provided for a surgeon. Moreover, with the unique full V-shaped structures design, the surgeon can guarantee that bone grooves at a hinge side after grinding form fully closed V-shaped grooves at any operating angle, thereby reducing the area of an incision window, facilitating the use by a surgeon and improving the surgical efficiency.

14 Claims, 8 Drawing Sheets

(52) U.S. Cl.
CPC ............. *A61B 2017/320004* (2013.01); *A61B 2017/320072* (2013.01); *A61B 2017/320084* (2013.01)

(58) Field of Classification Search
CPC ........ A61B 17/1659; A61B 2017/1602; A61B 2017/320004; A61B 2017/320068; A61B 2017/320072
See application file for complete search history.

(56) References Cited

U.S. PATENT DOCUMENTS

| | | | |
|---|---|---|---|
| 2006/0004396 A1 | 1/2006 | Easley et al. | |
| 2008/0058775 A1 | 3/2008 | Darian et al. | |
| 2008/0085488 A1* | 4/2008 | Lazarof | A61C 8/0089 433/50 |
| 2009/0326535 A1 | 12/2009 | Blus | |
| 2012/0165809 A1 | 6/2012 | Christian et al. | |
| 2015/0005774 A1 | 1/2015 | Voic et al. | |
| 2016/0192982 A1 | 7/2016 | Just et al. | |
| 2017/0119404 A1* | 5/2017 | Ueda | A61B 17/1675 |
| 2019/0269469 A1* | 9/2019 | Bush, Jr. | A61B 34/76 |
| 2022/0241091 A1* | 8/2022 | Greenhalgh | A61B 17/1671 |

FOREIGN PATENT DOCUMENTS

| | | | | |
|---|---|---|---|---|
| CN | 203790000 U | 8/2014 | | |
| CN | 105451671 A | 3/2016 | | |
| CN | 205964114 U | 2/2017 | | |
| CN | 107320151 A | 11/2017 | | |
| CN | 107744401 A | 3/2018 | | |
| CN | 208942274 U | 6/2019 | | |
| EP | 0456470 A1 | 11/1991 | | |
| EP | 3130306 A1 | 2/2017 | | |
| JP | 2013538615 A | 10/2013 | | |
| KR | 20050105272 A | 11/2005 | | |
| KR | 20160000984 U | 3/2016 | | |
| KR | 20180044934 A | 5/2018 | | |
| KR | 20190001034 U | 5/2019 | | |
| WO | WO-2004014241 A1 * | 2/2004 | ......... | A61B 17/1615 |
| WO | WO-2015145444 A2 * | 10/2015 | ......... | A61B 10/0266 |

OTHER PUBLICATIONS

PCT/CN2018/105781, "International Preliminary Report on Patentability", dated May 28, 2020, 11 pages.

* cited by examiner

ULTRASONIC OSTEOTOME BIT

CROSS-REFERENCE TO RELATED APPLICATIONS

This application is a U.S. National Stage of International Application No. PCT/CN2018/105781, filed Sep. 14, 2018, which claims the benefit of Chinese Patent Application No. 201711118873.2, filed Nov. 14, 2017. The contents of these applications are hereby incorporated by reference in their entireties for all purposes.

TECHNICAL FIELD

The present disclosure relates to the technical field of medical instruments, and in particular to an ultrasonic osteotome bit.

BACKGROUND ART

In orthopedic surgery, an ultrasonic osteotome is often used to perform cutting, grinding, shaving, scraping or any shaping on bones. Most of the ultrasonic osteotome bits currently used for bone-grinding are square or circular. FIG. 1 shows a circular ultrasonic osteotome bit in the prior art, comprising a bit body 3', a bit bar 1' and a circular bit grinding portion 2'. The ultrasonic osteotome bit is provided, on a lateral side, with teeth to increase the friction area and resistance and further improve the cutting efficiency.

The application of such an ultrasonic osteotome bit in spine surgery has the following problems: the bone face after grinding is of a flat square or circular shape, so that in an operation that requires forming grooves and grinding bones, the amount of bone to be removed is large, and the operation speed is slow; and in a specific operation, such as single-door laminoplasty of cervical vertebrae, during grinding of a hinge side, due to its shape, the bone faces after grinding cannot be in close contact when closed, which increases the healing time of the patient and is prone to inducing some other complications in the formed cavity.

SUMMARY

The present disclosure provides an ultrasonic osteotome bit, comprising a bit bar, a bit body, and a bit grinding portion located at a front end of the ultrasonic osteotome bit. The bit grinding portion is in the shape of a triangular pyramid, the bottom face of the triangular pyramid is a rear end of the bit grinding portion, and the tip of the triangular pyramid directly facing the bottom face is the front end of the bit grinding portion. One end of the bit bar is connected to the rear end of the bit grinding portion, and the other end of the bit bar is connected to the bit body. Two of the three lateral pyramidal faces of the triangular pyramid are respectively used as a first grinding face and a second grinding face. By means of the ultrasonic osteotome bit, a normal bone-grinding operation can be completed, and since the front end thereof is small in area, the grinding speed is high. In addition, owing to the design in which the front end is small while the rear end is large, a good visual field can be provided for a surgeon. Moreover, since the unique full V-shaped structures design are used, the surgeon can guarantee that bone grooves at a hinge side after grinding form fully closed V-shaped grooves at any operating angle, thereby reducing the area of an incision window, facilitating the use by a surgeon and improving the surgical efficiency.

In an embodiment of the ultrasonic osteotome bit of the present disclosure, a grinding edge is formed between the first grinding face and the second grinding face; on the first grinding face, the distances from any two points on the grinding edge to a first base vertex facing the grinding edge are approximately equal to each other; and on the second grinding face, the distances from any two points on the grinding edge to a second base vertex facing the grinding edge are approximately equal to each other.

In an embodiment of the ultrasonic osteotome bit of the present discourse, the distance from any point on the grinding edge to the first base vertex is substantially equal to the distance from the point to the second base vertex.

In an embodiment of the ultrasonic osteotome bit of the present disclosure, a front portion of the grinding edge is a smooth flat surface or a slightly raised curved surface, the first grinding face and/or the second grinding face is an arc-shaped face protruding outward, and a smooth arc transition is provided between the first grinding face and the second grinding face.

In an embodiment of the ultrasonic osteotome bit of the present disclosure, the first grinding face and the second grinding face are provided with a plurality of grinding grooves, file teeth or knurled teeth.

In an embodiment of the ultrasonic osteotome bit of the present disclosure, the grinding groove has a certain width, and the edge of the grinding groove is provided with a reverse fine edge.

In an embodiment of the ultrasonic osteotome bit of the resent disclosure, the ultrasonic osteotome bit further comprises a hollow liquid injection channel, wherein the hollow liquid injection channel passes from the other end of the bit bar to the bit grinding portion along a direction of the center line of the bit bar, the bit grinding portion is provided with a transverse liquid guide channel that transversely passes along an axis substantially perpendicular to the bit bar, the transverse liquid guide channel is in communication with the hollow liquid injection channel, and the transverse liquid guide channel forms openings in the first grinding face and the second grinding face.

In an embodiment of the ultrasonic osteotome bit of the present disclosure, the center line of the bit bar is a curve that bends towards one side of the bit bar.

In an embodiment of the ultrasonic osteotome bit of the resent disclosure, the center line of the bit body is a curve that bends towards one side of the bit body.

In an embodiment of the ultrasonic osteotome bit of the present disclosure, the joint between the bit bar and the bit body is a tapered face that gradually reduces from the bit body to the bit bar.

According to the technical solution of the present disclosure, by means of designing the bit grinding portion of the ultrasonic osteotome bit to be a triangular pyramid, a normal bone-grinding operation can be completed, and since the front end thereof is small in area, the grinding speed is high. In addition, owing to the design in which the front end is small while the rear end is large, a good visual field can be provided for a surgeon. Moreover, with the unique full V-shaped structures design, the surgeon can guarantee that bone grooves at a hinge side after grinding fully closed V-shaped grooves at any operating angle, thereby reducing the incision area of a window, facilitating the use by a surgeon and improving the surgical efficiency.

BRIEF DESCRIPTION OF THE DRAWINGS

In order to describe the technical solutions in the specific embodiments of the present disclosure or in the prior art more clearly, the accompanying drawings to be used for the description of the specific embodiments or the prior art will be briefly introduced below. Obviously, the accompanying drawings in the following description show some embodiments of the present disclosure, and those of ordinary skill in the art would have derived other drawings from these accompanying drawings without any creative effort.

REFERENCE NUMERALS

Figure 1:
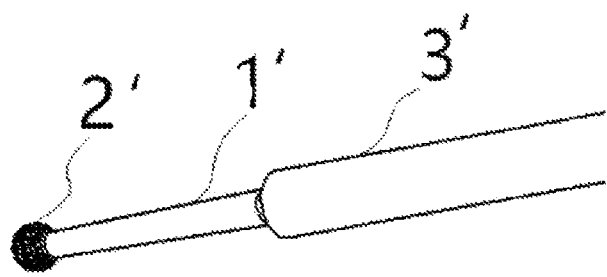
FIG. 1 is a perspective view of an ultrasonic osteotome bit in the prior art.
Figure 2:
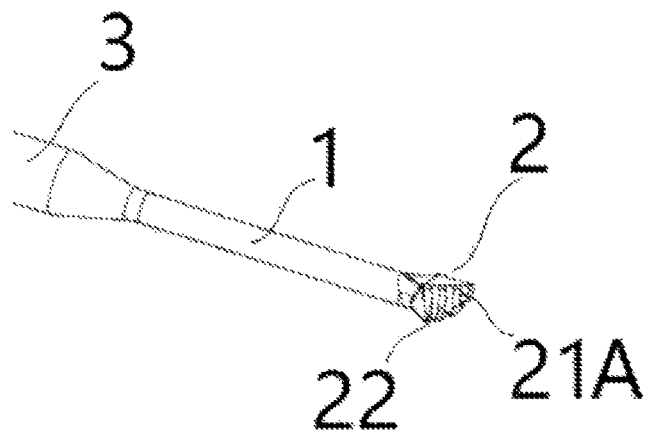
FIG. 2 is a perspective view of an ultrasonic osteotome bit according to a first embodiment of the present disclosure.
Figure 3:
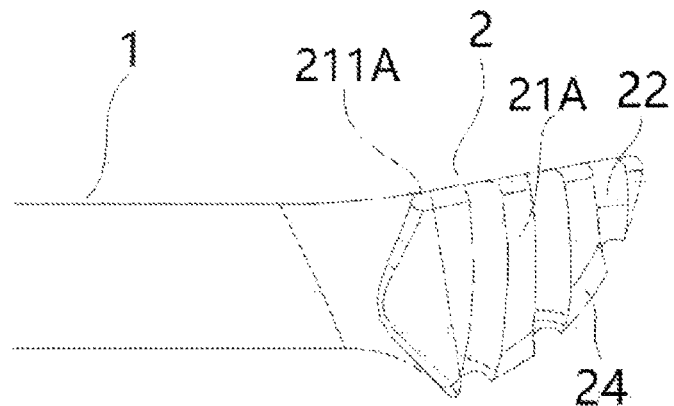
FIG. 3 is a side view of the ultrasonic osteotome bit according to the first embodiment of the present disclosure.
Figure 4:
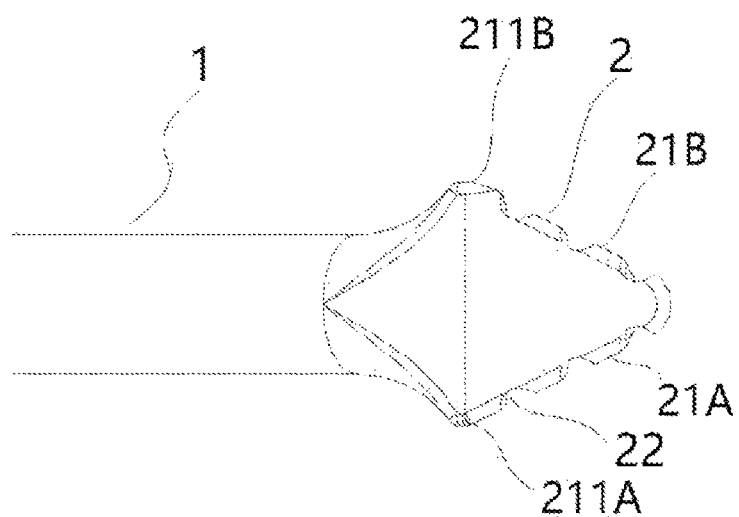
FIG. 4 is a top view of the ultrasonic osteotome bit according to the first embodiment of the present disclosure.

1', 1—bit bar; 2', 2—bit grinding portion; 3', 3—bit body; 10—hollow liquid injection channel; 20—transverse liquid guide channel; 21A—first grinding face; 21B—second grinding face; 22—grinding groove; 23—file tooth; 24—grinding edge; 211A—first base vertex; 211B—second base vertex.

DETAILED DESCRIPTION OF EMBODIMENTS

In order to make the objectives, technical solutions and advantages of the present disclosure clearer, the technical solutions in the embodiments of the present disclosure will be clearly and completely described below in conjunction with the drawings in the embodiments of the present disclosure, and it should be understood that the specific embodiments described herein are merely illustrative of the present disclosure, but are not intended to limit the present disclosure. The embodiments described are merely a part rather than all of the embodiments of the present disclosure. Based on the embodiments of the present disclosure, all other embodiments which would have been obtained by those of ordinary skill in the art without any creative effort shall fall within the scope of protection of the present disclosure.

In the description of the present disclosure, it should be noted that the orientation or positional relationship indicated by the terms "top", "bottom", "front", "rear", "transverse", "axial", etc. are based on the orientation or positional relationship shown in the drawings, and are intended to facilitate the description of the present disclosure and simplify the description only, rather than indicating or implying that the devices or elements referred to must have particular orientations or be constructed and operated in particular orientations, thus will not be interpreted as limiting the present disclosure.

Furthermore, in the description of the present disclosure, it should be noted that the terms, "connecting" and "connection" should be understood in a broad sense, unless otherwise explicitly specified or defined, for example, it may be a fixed connection, a detachable connection or an integrated connection; may be a mechanical connection or an electrical connection; and may be a direct connection or an indirect connection through an intermediate medium, or may be a communication between the interior of two elements. For those of ordinary skill in the art, the specific meaning of the terms mentioned above in the present disclosure should be construed according to specific circumstances.

FIGS. 2 to 14 show an ultrasonic osteotome bit of the present disclosure. As shown in the figures, the ultrasonic osteotome bit of the present disclosure comprises a bit bar 1, a bit body 3, and a bit grinding portion 2 located at a front end of the ultrasonic osteotome bit. The bit grinding portion 2 is in the shape of a triangular pyramid, the bottom face of the triangular pyramid is a rear end of the bit grinding portion 2, and the tip of the triangular pyramid directly facing the bottom face is a front end of the bit grinding portion 2. One end of the bit bar 1 is connected to the rear end of the bit grinding portion 2, and the other end of the bit bar 1 is connected to the bit body 3. Two of the three lateral pyramidal faces of the triangular pyramid are respectively used as a first grinding face 21A and a second grinding face 21B. The first grinding face 21A and the second grinding face 21B are used for grinding bones.

According to the present disclosure, by means of designing the bit grinding portion 2 of the ultrasonic osteotome bit to be a triangular pyramid, the normal bone-grinding operation can be completed by the ultrasonic osteotome bit, and moreover, since the front end thereof is small in area, the grinding speed is high. In addition, since the front end is small while the rear end is large, a good visual field can be provided for a surgeon. Moreover, the triangular pyramid has a plurality of V-shaped structures. With unique full V-shaped structures in the present application, the surgeon can guarantee that bone grooves at a hinge side after grinding form fully closed V-shaped grooves at any operating angle, thereby reducing the area of an incision window, facilitating the use by a surgeon and improving the surgical efficiency.

A grinding edge 24 is formed between the first grinding face 21A and the second grinding face 21B, and the grinding edge 24 may be used to cut underlying tissues. On the first grinding face 21A, the distances from any two points on the grinding edge 24 to a first base vertex 211A facing the grinding edge 24 are approximately equal to each other; and on the second grinding face 21B, the distances from any two points on the grinding edge 24 to a second base vertex 211B facing the grinding edge 24 are approximately equal to each other. According to the design of the present disclosure, during the operation, whether the bit is operated vertically or horizontally, the incisions are substantially the same V-shaped incision. That is, the operator can guarantee that the cutting grooves are all V-shaped by operating the grinding portion at any angle along the cutting direction of the bit during a surgical operation. In addition, during bone-grinding, the force is substantially uniform at any point on the grinding edge 24 on one side of the first grinding face 21A, and the force is substantially uniform at any point on the grinding edge 24 on one side of the second grinding face 21B.

The distance from any point on the grinding edge 24 to the first base vertex 211A is substantially equal to the distance from the point to the second base vertex 211B. With such a design, during bone-grinding, the force is substantially uniform at any point on the grinding edge 24 on one side of the first grinding face 21A and the second grinding face 21B. The grinding edge 24 is arc-shaped, and on the first grinding face 21A, the center of the arc is the first base vertex 211A; and on the second grinding face 21B, the center of the arc is the second base vertex 211B.

Wherein, both the first grinding face 21A and the second grinding face 21B may be a flat surface. That is, the bit grinding portion 2 is in the shape of a normal triangular pyramid composed of four triangles. However, the present disclosure is not limited thereto. FIGS. 2 to 5 show an ultrasonic osteotome bit according to a first embodiment of the present disclosure. The bit grinding portion 2 may be in the shape of an abnormal triangular pyramid, i.e., the first grinding face 21A and/or the second grinding face 21B may be an arc-shaped face protruding outward, thereby being able to adapt to different grinding situations.

Figure 5:
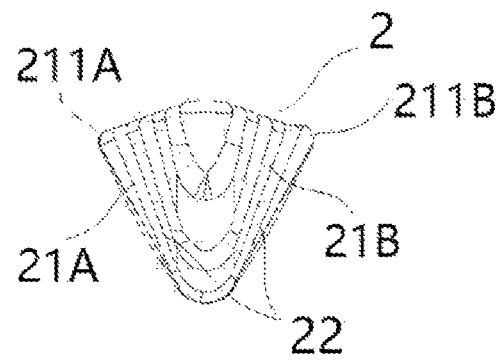
FIG. 5 is a front view of the ultrasonic osteotome bit according to the first embodiment of the present disclosure.

In the actual operation, some bone-grinding operations need to protect the underlying soft tissues. Accordingly, a front portion of the grinding edge 24 is a smooth flat surface or a slightly raised curved surface, so that the underlying soft tissues are not damaged. As shown in FIG. 5, the tip of the triangular pyramid directly facing the bottom face is also configured to be a smooth flat surface or curved surface so as to further prevent the soft tissues in front of and below the bit grinding portion 2 from being damaged.

In the first embodiment of the present disclosure, as shown in FIG. 5, a smooth arc transition is provided between the first grinding face 21A and the second grinding face 21B. Thus, the ultrasonic osteotome bit is safer in use, and moreover, it is possible to prevent the soft tissues in front of and below the bit grinding portion 2 from being damaged.

In the first embodiment of the present disclosure, as shown in FIGS. 2 to 5, the first grinding face 21A and/or the second grinding face 21B may be provided with a plurality of grinding grooves 22. The plurality of grinding grooves 22 are arranged parallel to each other, and the grinding grooves 22 are transverse grooves perpendicular to the center line of the ultrasonic osteotome bit. However, the present disclosure is not limited thereto. The grinding grooves 22 may also be diagonal grooves that form a certain angle with the center line of the ultrasonic osteotome bit.

The grinding groove 22 has a certain width, and the edge of the grinding groove 22 is provided with a reverse fine-bladed edge, which facilitates scraping while grinding and improves the bone-grinding efficiency of the bit grinding portion 2.

Figure 6:
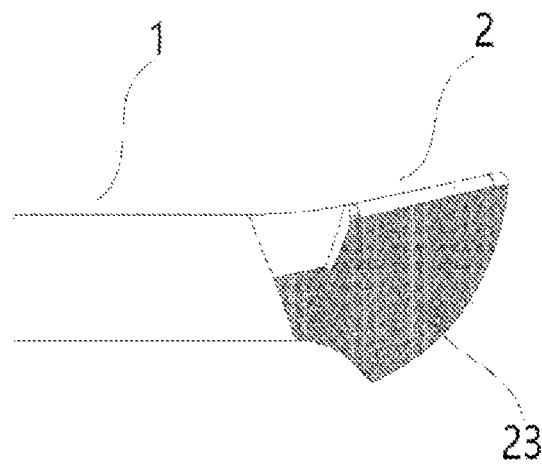
FIG. 6 is a side view of an ultrasonic osteotome bit according to a second embodiment of the present disclosure.
Figure 7:
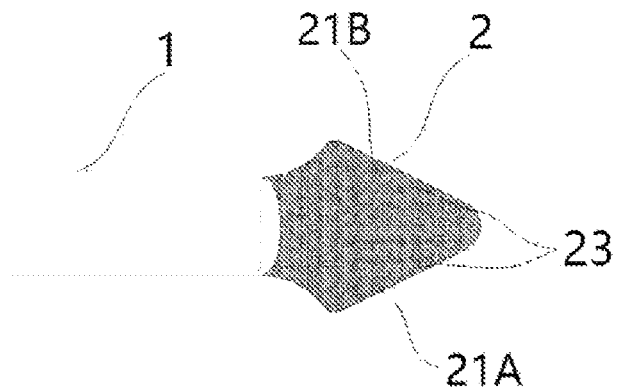
FIG. 7 is a bottom view of the ultrasonic osteotome bit according to the second embodiment of the present disclosure.
Figure 8:
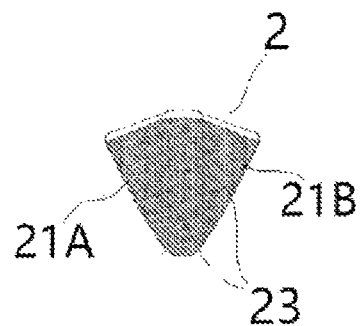
FIG. 8 is a front view of the ultrasonic osteotome bit according to the second embodiment of the present disclosure.
Figure 9:
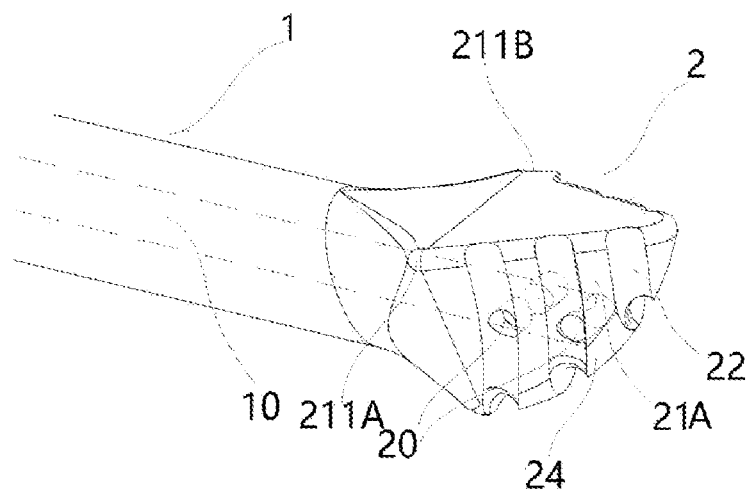
FIG. 9 is a perspective view of an ultrasonic osteotome bit according to a third embodiment of the present disclosure.
Figure 10:
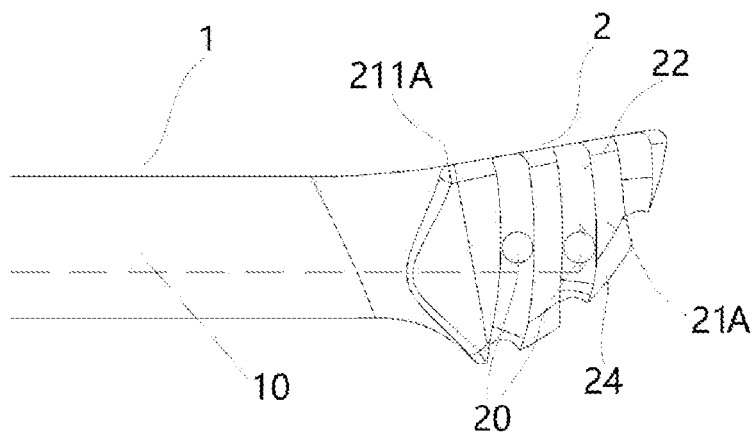
FIG. 10 is a side view of the ultrasonic osteotome bit according to the third embodiment of the present disclosure.
Figure 11:
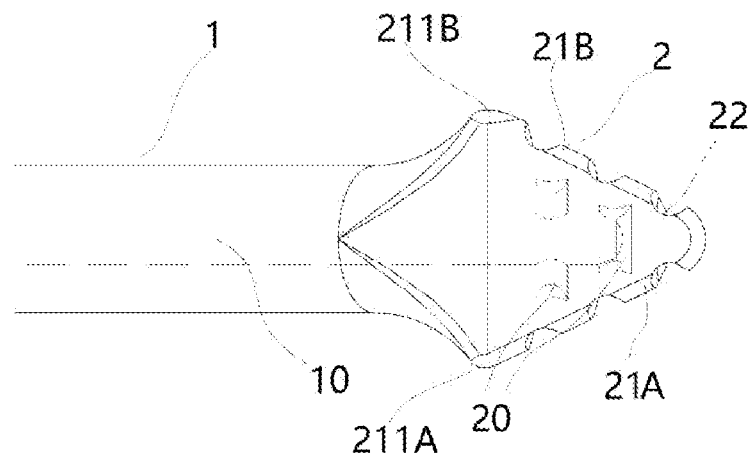
FIG. 11 is a top view of the ultrasonic osteotome bit according to the third embodiment of the present disclosure.
Figure 12:
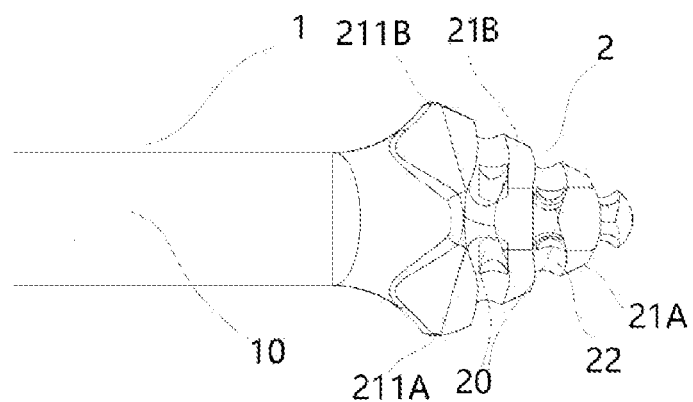
FIG. 12 is a bottom view of the ultrasonic osteotome bit according to the third embodiment of the present disclosure.

FIGS. 6 to 8 show an ultrasonic osteotome bit according to a second embodiment of the present disclosure. The ultrasonic osteotome bit according to the second embodiment of the present disclosure only differs from the ultrasonic osteotome bit according to the first embodiment in that the first grinding face 21A and/or the second grinding face 21B is provided with a plurality of file teeth 23. The first grinding face 21A and/or the second grinding face 21B provided with the file teeth 23 is better in hemostatic effect and safer. However, the present disclosure is not limited thereto, and the two grinding faces 21 may be provided with a knurled structure.

FIGS. 9 to 12 show an ultrasonic osteotome bit according to a third embodiment of the present disclosure. The ultrasonic osteotome bit according to the third embodiment of the present disclosure only differs from the ultrasonic osteotome bit according to the first embodiment of the present disclosure in that the ultrasonic osteotome bit further includes a hollow liquid injection channel 10, wherein the hollow liquid injection channel 10 passes from the other end of the bit bar 1 to the bit grinding portion 2 along a direction of the center line of the bit bar 1. The bit grinding portion 2 is provided with a transverse liquid guide channel 20 that transversely passes along an axis substantially perpendicular to the bit bar 1, the transverse liquid guide channel 20 is in communication with the hollow liquid injection channel 10, and the transverse liquid guide channel 20 forms openings in the first grinding face 21A and the second grinding face 21B.

In the ultrasonic osteotome bit according to the third embodiment of the present disclosure, the structural characteristics of the bit are fully used, and by means of providing an axial hollow liquid injection channel 10 on the bit bar 1 and providing a transverse liquid guide channel 20 on the bit grinding portion 2, the ultrasonic cooling liquid can pass through the hollow liquid injection channel 10, flow out of the opening of the transverse liquid guide channel 20, and sufficiently flow to the bit without being scattered by the excitation of ultrasonic vibration. Thus, the bit grinding portion 2 is sufficiently cooled and washed in use.

Furthermore, in order to achieve a better operating angle of the ultrasonic osteotome bit, in the first embodiment of the present disclosure, the bit grinding portion 2 may incline upward along the bit bar 1 or the bit body 3 at a certain angle to obtain a better operating space.

Figure 13:
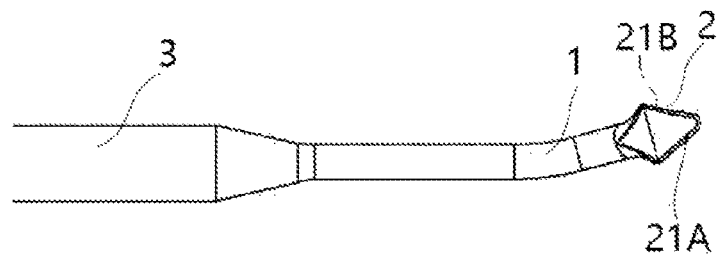
FIG. 13 is a perspective view of an ultrasonic osteotome bit according to a fourth embodiment of the present disclosure.

FIG. 13 shows an ultrasonic osteotome bit according to a fourth embodiment of the present disclosure. The ultrasonic osteotome bit according to the fourth embodiment of the present disclosure differs from the first embodiment in that the center line of the bit bar 1 is a curve that bends towards one side of the bit bar 1.

Figure 14:
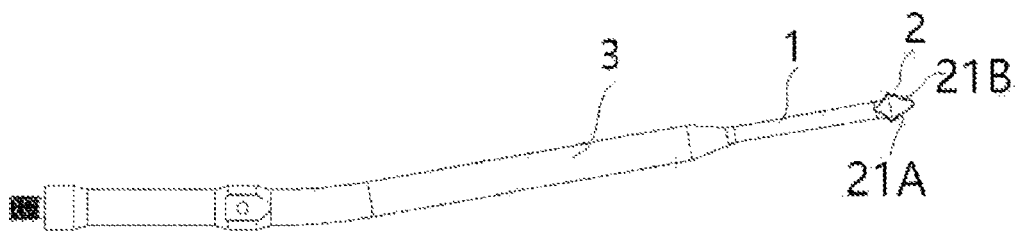
FIG. 14 is a perspective view of an ultrasonic osteotome bit according to a fifth embodiment of the present disclosure.

FIG. 14 shows an ultrasonic osteotome bit according to a fifth embodiment of the present disclosure. The ultrasonic osteotome bit according to the fifth embodiment of the present disclosure differs from the fourth embodiment in that the center line of the bit body 3 is a curve that bends towards one side of the bit body 3. The ultrasonic osteotome bit shown in FIG. 14 is also provided, on the bit body 3, with an axial hollow liquid injection channel 10 and a transverse liquid guide channel 20 and is provided with openings in a circumferential face of the bit body 3. In order to furthest ensure that the liquid flow of ultrasonic cooling liquid reaches the top of the bit through the V-shaped structures of the triangular pyramid, the joint between the bit bar 1 and the bit body 3 is a tapered face that gradually reduces from the bit body 3 to the bit bar 1.

In an embodiment of the ultrasonic osteotome bit of the present disclosure, one end of the bit body 3 may be connected to the bit bar 1 through the tapered face, the other end of the bit body 3 is a threaded connection end which may be connected to a specific ultrasonic transducer by means of threaded connection, and then the ultrasonic transducer is connected to a specific ultrasonic host for operation.

Figure 15:
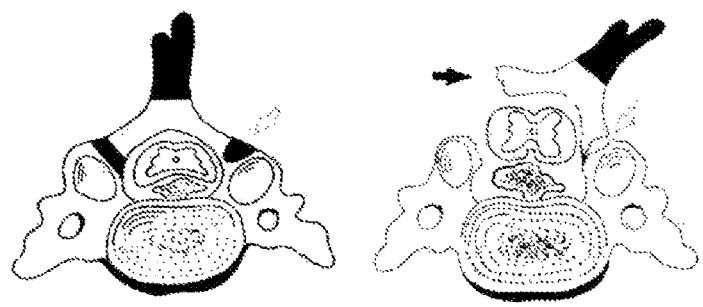
FIG. 15 is a schematic diagram of an operation result using the ultrasonic osteotome bit of the prior art in single-door laminoplasty.

FIG. 15 shows a schematic diagram of an operation result using the ultrasonic osteotome bit of the prior art in single-door laminoplasty. Referring to the grinding operation in FIG. 15, in the single-door laminoplasty of cervical vertebra, during grinding of a hinge side, since the bit grinding portion is square or circular, the bone faces after grinding cannot be in close contact when closed, which increases the healing time of the patient and is prone to inducing some other complications in the cavity formed.

Figure 16:
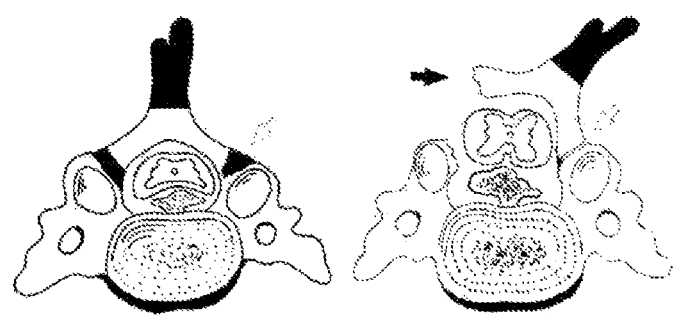
FIG. 16 is a schematic diagram of an operation result using the ultrasonic osteotome bit of the present disclosure in single-door laminoplasty.

FIG. 16 shows a schematic diagram of an operation result using the ultrasonic osteotome bit of the present disclosure in single-door laminoplasty. As shown in FIG. 16, after an operation which is performed using the ultrasonic osteotome bit of the present disclosure, the bone faces after grinding are relatively regular, so that it can be ensured that the bone faces after grinding are in close contact when closed, which achieves high fitness of the surface of a wound, facilitates the bone healing, reduces the risk of inducing complications, and allows the patient to have less pain after surgery and recover rapidly. In addition, with the use of the ultrasonic osteotome bit of the present disclosure, the amount of bone to be removed is reduced, and the healing time of the patient is shortened.

In summary, according to the present disclosure, by means of designing the bit grinding portion 2 of the ultrasonic osteotome bit to be a triangular pyramid, the normal bone-grinding operation can be completed by the ultrasonic osteotome bit. Also, since the front end thereof is small in area, the grinding speed is high. In addition, owing to the design in which the front end is small while the rear end is large, a good visual field can be provided for a surgeon. Moreover, the triangular pyramid has a plurality of V-shaped structures. With unique full V-shaped structures in the present application, the surgeon can guarantee that bone grooves at a hinge side after grinding form fully closed V-shaped grooves at any operating angle along the bit-grinding direction, thereby reducing the area of an incision window, facilitating the use by a surgeon and improving the surgical efficiency and safety. In addition, owing to the less amount of bone to be removed, the healing time of the patient is shortened.

The above descriptions are merely the specific embodiments of the present disclosure, but the scope of protection of the present disclosure is not limited thereto, and any changes or substitutions readily made by those skilled in the art within the technical scope disclosed in the present disclosure should be all intended to be included within the scope of protection of the present disclosure.

The invention claimed is:

1. An ultrasonic osteotome bit, comprising a bit bar (1), a bit body (3), and a bit grinding portion (2) located at a front end of the ultrasonic osteotome bit, wherein
the bit grinding portion (2) is in the shape of a triangular pyramid, a bottom face of the triangular pyramid is a rear end of the bit grinding portion (2), and a tip of the triangular pyramid directly facing the bottom face is a front end of the bit grinding portion (2); one end of the bit bar (1) is connected to the rear end of the bit grinding portion (2), and the other end of the bit bar (1) is connected to the bit body (3); and two of the three lateral pyramidal faces of the triangular pyramid are respectively used as a first grinding face (21A) and a second grinding face (21B);
wherein:
a grinding edge (24) is formed between the first grinding face (21A) and the second grinding face (21B); on the first grinding face (21A), the distances from any two points on the grinding edge (24) to a first base vertex (211A) facing the grinding edge (24) are approximately equal to each other; and
on the second grinding face (21B) the distances from any two points on the grinding edge (24) to a second base vertex (211B) facing the grinding edge (24) are approximately equal to each other.

2. The ultrasonic osteotome bit according to claim 1, wherein
the distance from any point on the grinding edge (24) to the first base vertex (211A) is substantially equal to the distance from the point to the second base vertex (211B).

3. The ultrasonic osteotome bit according to claim 1, wherein
a front portion of the grinding edge (24) is a smooth flat surface or a slightly raised curved surface, the first grinding face (21A) and/or the second grinding face (21B) is an arc-shaped face protruding outward, and a smooth arc transition is provided between the first grinding face (21A) and the second grinding face (21B).

4. The ultrasonic osteotome bit according to claim 1, wherein
the first grinding face (21A) and/or the second grinding face (21B) are provided with a plurality of grinding grooves (22), file teeth (23) or knurled teeth.

5. The ultrasonic osteotome bit according to claim 4, wherein
each grinding groove (22) has a width, and an edge of each grinding groove (22) is provided with a reverse fine edge.

6. The ultrasonic osteotome bit according to claim 4, wherein
the plurality of grinding grooves (22) are arranged parallel to each other, and the grinding grooves (22) are transverse grooves perpendicular to a center line of the ultrasonic osteotome bit; or
the plurality of grinding grooves (22) are diagonal grooves that form an angle with the center line of the ultrasonic osteotome bit.

7. The ultrasonic osteotome bit according to claim 1, wherein
the ultrasonic osteotome bit further comprises a hollow liquid injection channel (10), and the hollow liquid injection channel (10) passes from the other end of the bit bar (1) to the bit grinding portion (2) in a direction of a center line of the bit bar (1), the bit grinding portion (2) is provided with a transverse liquid guide channel (20) that transversely passes along an axis substantially perpendicular to the bit bar (1), the transverse liquid guide channel (20) is in communication with the hollow liquid injection channel (10), and the transverse liquid guide channel (20) forms openings in the first grinding face (21A) and the second grinding face (21B).

8. The ultrasonic osteotome bit according to claim 7, wherein the center line of the bit bar (1) is a curve that bends towards one side of the bit bar (1).

9. The ultrasonic osteotome bit according to claim 7, wherein the center line of the bit body (3) is a curve that bends towards one side of the bit body (3).

10. The ultrasonic osteotome bit according to claim 1, wherein a joint between the bit bar (1) and the bit body (3) is a tapered face that gradually reduces from the bit body (3) to the bit bar (1).

11. The ultrasonic osteotome bit according to claim 1, wherein the grinding edge (24) is arc-shaped, and on the first grinding face (21A), a center of the arc is the first base vertex (211A); and on the second grinding face (21B), the center of the arc is the second base vertex (211B).

12. The ultrasonic osteotome bit according to claim 1, wherein the bit grinding portion (2) inclines upward along the bit bar (1) or the bit body (3) at an angle.

13. The ultrasonic osteotome bit according to claim 1, wherein the tip of the triangular pyramid directly facing the bottom face is configured to be a smooth flat surface or curved surface.

14. The ultrasonic osteotome bit according to claim 1, wherein both the first grinding face (21A) and the second grinding face (21B) are flat surfaces.

* * * * *